US011166674B2

(12) United States Patent
Namkoong et al.

(10) Patent No.: US 11,166,674 B2
(45) Date of Patent: *Nov. 9, 2021

(54) WRIST-TYPE BODY COMPOSITION MEASURING APPARATUS

(71) Applicant: SAMSUNG ELECTRONICS CO., LTD., Suwon-si (KR)

(72) Inventors: Kak Namkoong, Seoul (KR); Young Jun Koh, Seoul (KR); Yeol Ho Lee, Anyang-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/636,244

(22) Filed: Jun. 28, 2017

(65) Prior Publication Data
US 2017/0296120 A1 Oct. 19, 2017

Related U.S. Application Data

(63) Continuation-in-part of application No. 15/211,642, filed on Jul. 15, 2016, now abandoned.

(30) Foreign Application Priority Data

Dec. 29, 2015 (KR) .................. 10-2015-0188853

(51) Int. Cl.
*A61B 5/00* (2006.01)
*A61B 5/0408* (2006.01)
(Continued)

(52) U.S. Cl.
CPC ............ *A61B 5/681* (2013.01); *A61B 5/0059* (2013.01); *A61B 5/0537* (2013.01); *A61B 5/282* (2021.01); *A61B 5/7282* (2013.01); *A61B 5/742* (2013.01)

(58) Field of Classification Search
None
See application file for complete search history.

(56) References Cited

U.S. PATENT DOCUMENTS

| | | |
|---|---|---|
| 1,179,997 A | 4/1916 | Berry |
| 7,894,888 B2 | 2/2011 | Chan et al. |

(Continued)

FOREIGN PATENT DOCUMENTS

| | | |
|---|---|---|
| JP | 11-299752 A | 11/1999 |
| JP | 2001-070275 A | 3/2001 |

(Continued)

OTHER PUBLICATIONS

JP2001149329A—Machine Translation.*

*Primary Examiner* — Sean P Dougherty
*Assistant Examiner* — Benjamin S Melhus
(74) *Attorney, Agent, or Firm* — Sughrue Mion, PLLC

(57) ABSTRACT

A wrist-type body composition measuring apparatus is provided to measure body composition conveniently. The wrist-type body composition measuring apparatus includes a main body comprising a measurer configured to measure body impedance of a user, and an analyzer configured to analyze a body composition of the user based on the measured body impedance; a strap connected to the main body and configured to be flexible; a first inner electrode and a second inner electrode which are provided on a rear surface of the main body to be in direct contact with the user; and a first outer electrode and a second outer electrode which are provided on a surface of the main body to be in contact with the user during measurement of the body composition, wherein the first outer electrode and the second outer electrode are each formed as a half ring and face each other with a gap therebetween.

18 Claims, 16 Drawing Sheets

(51) Int. Cl.
*A61B 5/053* (2021.01)
*A61B 5/0537* (2021.01)
*A61B 5/282* (2021.01)

(56) References Cited

U.S. PATENT DOCUMENTS

| | | | |
|---|---|---|---|
| 9,049,998 B2 | 6/2015 | Brumback et al. | |
| 2003/0045802 A1* | 3/2003 | Kato | A61B 5/02438 |
| | | | 600/503 |
| 2010/0076331 A1* | 3/2010 | Chan | A61B 5/332 |
| | | | 600/522 |
| 2014/0288435 A1* | 9/2014 | Richards | A61B 5/14539 |
| | | | 600/479 |
| 2015/0119654 A1* | 4/2015 | Martin | A61B 5/318 |
| | | | 600/301 |
| 2015/0135310 A1* | 5/2015 | Lee | G06F 21/35 |
| | | | 726/20 |
| 2015/0173632 A1* | 6/2015 | Ma | A61B 5/0428 |
| | | | 600/324 |
| 2015/0366504 A1* | 12/2015 | Connor | A61B 5/6804 |
| | | | 600/301 |
| 2016/0029911 A1* | 2/2016 | Lee | A61B 5/02427 |
| | | | 600/301 |
| 2016/0058375 A1* | 3/2016 | Rothkopf | A61B 5/0205 |
| | | | 600/301 |
| 2016/0066812 A1* | 3/2016 | Cheng | A61B 5/024 |
| | | | 600/390 |
| 2016/0073914 A1* | 3/2016 | Lapetina | A61B 5/282 |
| | | | 600/384 |
| 2016/0089053 A1 | 3/2016 | Lee et al. | |
| 2016/0270668 A1* | 9/2016 | Gil | A61B 5/021 |
| 2017/0000415 A1* | 1/2017 | Lapetina | A61B 5/0205 |
| 2017/0020449 A1* | 1/2017 | Shim | A61B 5/7405 |
| 2017/0258349 A1* | 9/2017 | Watanabe | A61B 5/1118 |
| 2017/0347895 A1* | 12/2017 | Wei | A61B 5/01 |
| 2018/0014742 A1* | 1/2018 | Iwawaki | A61B 5/02 |

FOREIGN PATENT DOCUMENTS

| | | |
|---|---|---|
| JP | 2001-149329 A | 6/2001 |
| JP | 2001-252258 A | 9/2001 |
| JP | 2002-095637 A | 4/2002 |
| JP | 2002-355230 A | 12/2002 |
| KR | 10-0330746 B1 | 4/2002 |
| KR | 10-2003-0031246 A | 4/2003 |
| KR | 10-2016-0036958 A | 4/2016 |

* cited by examiner

WRIST-TYPE BODY COMPOSITION MEASURING APPARATUS

CROSS-REFERENCE TO RELATED APPLICATION

This application is a continuation-in-part of U.S. application Ser. No. 15/211,642, filed on Jul. 15, 2016, which claims priority from Korean Patent Application No. 10-2015-0188853, filed on Dec. 29, 2015 in the Korean Intellectual Property Office, the disclosures of which are incorporated herein by reference in their entireties.

BACKGROUND

1. Field

Apparatuses and methods consistent with exemplary embodiments relate to measuring biometric information of a user by using an apparatus wearable on the user's wrist.

2. Description of the Related Art

In the past, body composition was generally measured in hospitals for the purpose of medical check-up. However, with the recent improvement in living standards, and a growing interest in health and diet, people are keen to measure body composition in their daily lives and monitor body composition changes.

Measuring body composition refers to quantitative measurement of individual elements of body composition, such as water, proteins, bones, fat, and the like, which form the human body.

As a method of measuring body composition, bioelectrical impedance analysis is commonly used, which is cheap and harmless to humans. In the bioelectrical impedance analysis, a weak electric current is applied to the human body to calculate an amount of body water, muscles, body fat, and the like by using a value of electric resistance, i.e., the electrical impedance, of the human body, and information including a user's stature, weight, age, gender, and the like.

SUMMARY

One or more exemplary embodiments provide a wrist-type body composition measuring apparatus that may measure body composition conveniently while being carried.

According to an aspect of an exemplary embodiment there is provided a wrist-type body composition measuring apparatus including: a main body including a measurer configured to measure body impedance of a user, and an analyzer configured to analyze a body composition of the user based on the measured body impedance; a strap connected to the main body and configured to be flexible; a first inner electrode and a second inner electrode which are provided on a rear surface of the main body to be in direct contact with the user; and a first outer electrode and a second outer electrode which are provided on a surface of the main body to be in contact with the user during measurement of the body composition, wherein the first and second outer electrodes are each formed as a half ring and face each other with a gap therebetween.

Upon applying a current through the first inner electrode and the first outer electrode, the measurer may be further configured to measure a voltage through the second inner electrode and the second outer electrode to measure the body impedance.

The half ring may have an angular C-shape.

The half ring may have a semicircular shape.

The half ring may have a semielliptical shape or a semioval shape.

The half ring may be formed such that an inner portion has an angular shape and an outer portion has a curved shape.

The half ring may be formed such that an inner portion has a curved shape and an outer portion has an angular shape.

An arrangement direction of the first and second inner electrodes and an arrangement direction of the first and second outer electrodes may be perpendicular to a length direction of the strap.

An arrangement direction of the first and second inner electrodes and an arrangement direction of the first and second outer electrodes may be identical to a length direction of the strap.

One of an arrangement direction of the first and second inner electrodes and an arrangement direction of the first and second outer electrodes may be identical to a length direction of the strap and the other may be perpendicular to the length direction of the strap.

Upper surfaces of the first and second outer electrodes may be disposed on an identical plane.

The first and second outer electrodes may be configured to operate as function buttons to perform predetermined functions when the first and second outer electrodes are pressed.

The wrist-type body composition measuring apparatus may further comprise a bio-signal sensor disposed in a space between the first and second outer electrodes and configured to collect a bio-signal of the user.

The bio-signal may include a photoplethysmogram (PPG) signal.

The measurer may be further configured to measure an electrocardiography (ECG) signal through at least three electrodes selected from the first and second inner electrodes and the first and second outer electrodes.

Wrist-type body composition measuring apparatus may further comprise an electrocardiography (ECG) signal measurement circuit configured to measure an ECG signal through at least three electrodes selected from among the first inner electrode, the second inner electrode, the first outer electrode, and the second outer electrode.

The wrist-type body composition measuring apparatus may further comprise a bio-signal sensor disposed inside a space defined by inner portions of the first and second outer electrodes.

According to an aspect of an exemplary embodiment there is provided a wearable device comprising a first inner electrode and a second inner electrode electrically isolated from each other to be in direct contact with a user of the wearable device and a first outer electrode and a second outer electrode electrically isolated from each other and sized and arranged to be simultaneously touchable by a single finger of the user such that, when touched, the first outer electrode and the first inner electrode form a closed circuit through the user and the second outer electrode and the second inner electrode form a closed circuit through the user.

The wearable device may further include a bio-signal sensor surrounded by the first and second outer electrodes.

The first outer electrode may surrounds the second outer electrodes.

The first and second outer electrodes may face each other with a gap therebetween.

The wearable device may further comprise a bio-signal sensor disposed in a space between the first and second outer electrodes.

The bio-signal sensor may include a photoplethysmogram sensor.

The first outer electrode and the second outer electrode may have an angular C-shape, circular shape, or elliptical shape.

The first outer electrode and the second outer electrode may have an angular C-shape, semicircular shape, or semielliptical shape.

The wearable device may further comprise an electrocardiography (ECG) signal measurement circuit configured to measure an ECG signal through at least three of the first inner electrode, the second inner electrode, the first outer electrode and the second outer electrode.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
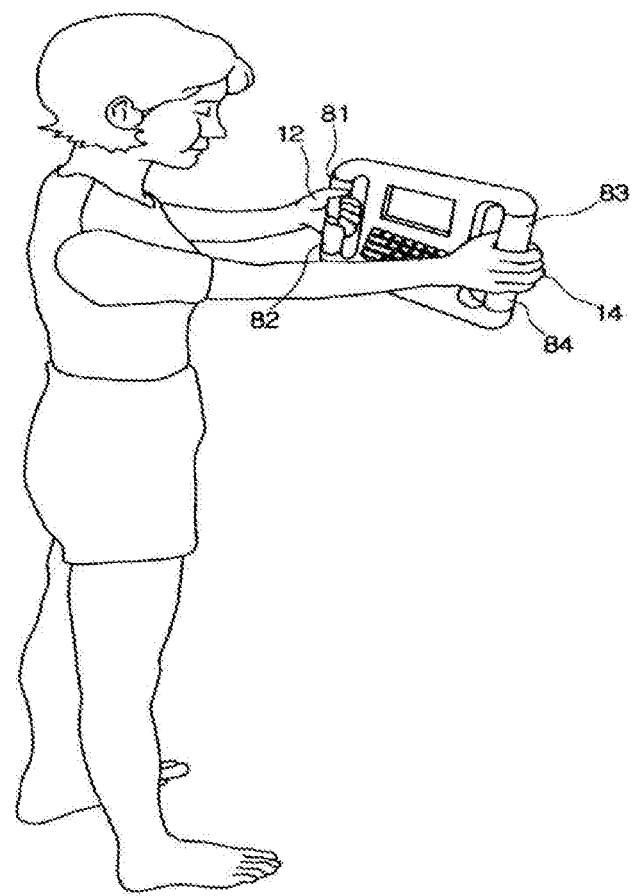
FIG. 1 is a diagram illustrating a general body composition measuring apparatus using bioelectrical impedance analysis.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a diagram illustrating a body composition measuring apparatus using bioelectrical impedance analysis in the related art. The body composition measuring apparatus is designed to measure body composition with both hands 12 and 14 holding electrodes 81, 82, 83, and 84. However, while carrying the apparatus, it may be inconvenient to use the apparatus, since both hands are required to hold the electrodes.

Figure 2:
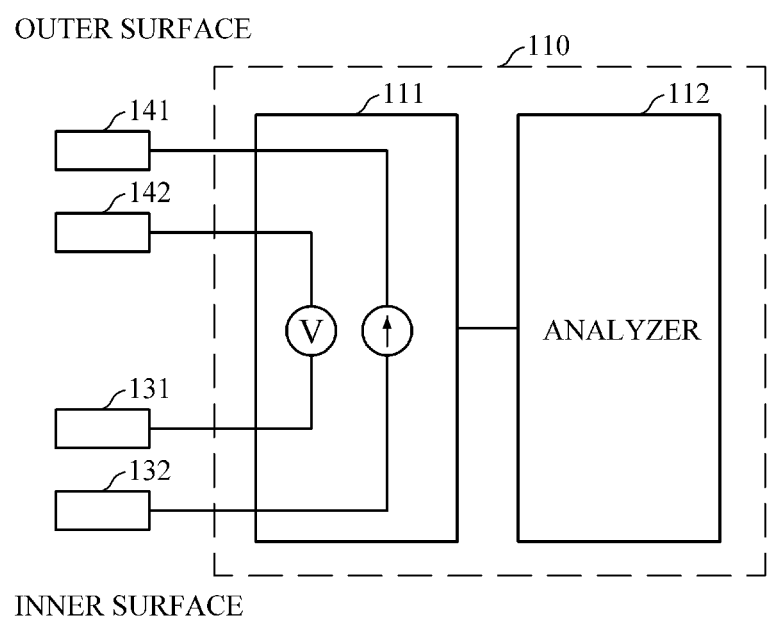
FIG. 2 is a block diagram illustrating an example of a wrist-type body composition measuring apparatus.
Figure 3:
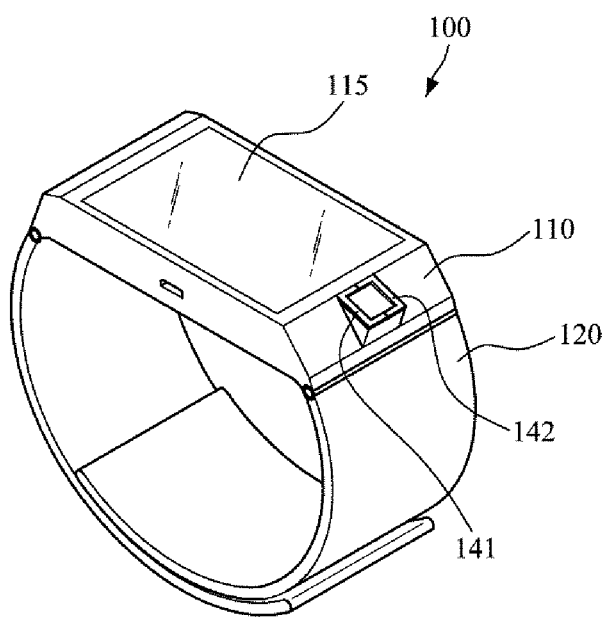
FIG. 3 is a perspective view illustrating an example of a wrist-type body composition measuring apparatus.

FIG. 2 illustrates a wrist-type body composition measuring apparatus 100 according to an exemplary embodiment. FIG. 3 is a perspective view illustrating the wrist-type body composition measuring apparatus 100, and FIG. 4 is a perspective view of the wrist-type body composition measuring apparatus 100 illustrated in FIG. 3, as seen from the rear side.

Figure 4:
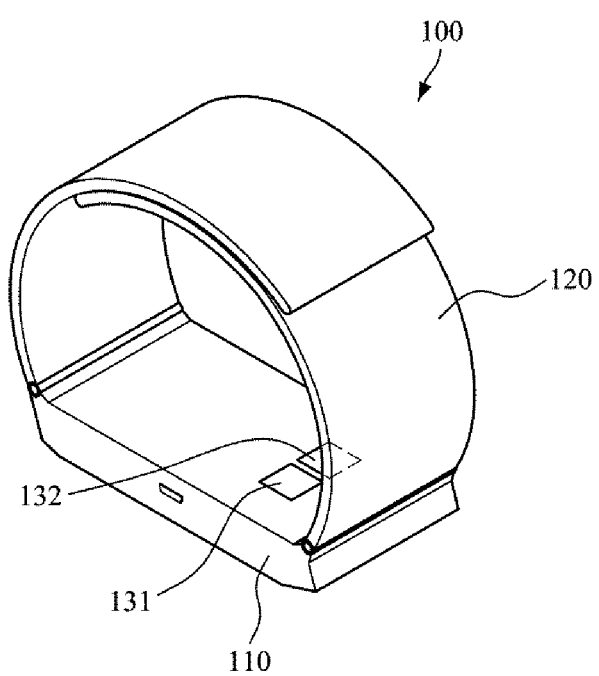
FIG. 4 is a perspective view of the wrist-type body composition measuring apparatus illustrated in FIG. 3, as seen from the rear side.

Referring to FIGS. 2 to 4, the wrist-type body composition measuring apparatus 100 includes a main body 110, a strap 120, a first inner electrode 131 and a second inner electrode 132, and a first outer electrode 141 and a second outer electrode 142.

The main body 110 includes a measurer 111 to measure body impedance and an analyzer 112 to analyze body composition of a user by using the body impedance measured by the measurer 111. Upon applying an alternating current between electrodes that are in contact with the body, the measurer 111 measures a voltage between the electrodes to calculate the body impedance. The alternating current may be a constant current of about 500 µA having a frequency of 50 kHz. Based on the measured body impedance, and stature, weight, age, and gender of a user, the analyzer 112 may calculate the total body water (TBW), body fat, and body fat percentage (%) using equations stored in the main body 110.

The strap 120 is connected to the main body 110, and is configured to be flexible. The strap 120 may be flexible enough to be wrapped around a user's wrist or may be unwrapped from the wrist, thereby enabling a user to put on or take off the wrist-type body composition measuring apparatus 100. The strap 120 may be made of urethane, silicone, rubber, leather, and the like.

The first and second inner electrodes 131 and 132 may be disposed on the rear surface of the main body 110 to be in direct contact with a user's body. That is, the first and second inner electrodes 131 and 132 may be in direct contact with a user's wrist. As illustrated in FIG. 4, the first and second inner electrodes 131 and 132 may be in a square shape. However, their shape is not limited thereto, and the first and second inner electrodes 131 and 132 may be in other shapes, for example, a rectangle, a lozenge, a circle, a triangle, and the like.

As illustrated in FIG. 4, the first and second inner electrodes 131 and 132 may be arranged perpendicular to a length direction of the main body 110 or a length direction of the strap 120, but the arrangement of the first and second inner electrodes 131 and 132 are not limited thereto.

Figure 5:
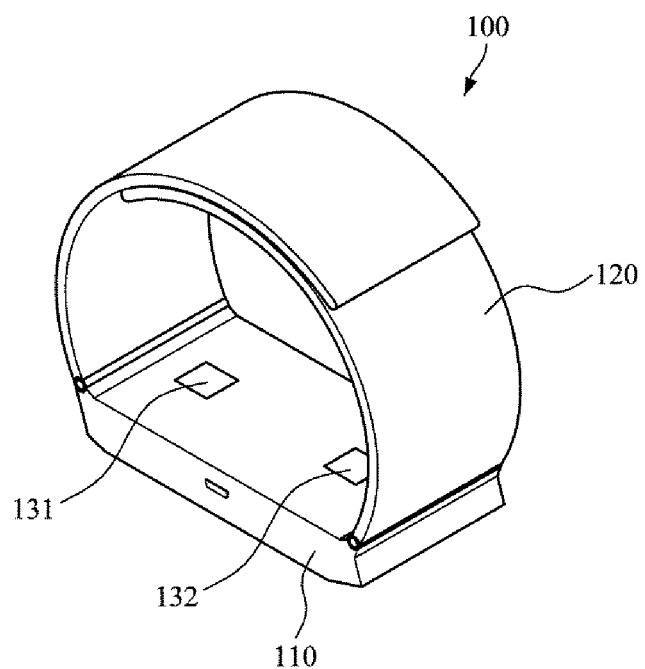
FIG. 5 is a perspective view of another example of the wrist-type body composition measuring apparatus, as seen from the rear side.

As shown in FIG. 5, the first inner electrode 131 and the second inner electrode 132 may be arranged to be apart from each other in the longitudinal direction of the main body 110.

The first and second outer electrodes 141 and 142 are disposed on the surface of the main body 110 to be in contact with a user during measurement of body composition, in which the first and second outer electrodes 141 and 142 are disposed close to each other to allow a user to contact both the first and second outer electrodes 141 and 142 with a finger. The second outer electrode 142 may have a circle shape and the first outer electrode 141 may have a ring shape that surrounds around the second outer electrode 142. The first and second outer electrodes 141 and 142 may have the same center point. As in the first and second inner electrodes 131 and 132, the first and second outer electrodes 141 and 142 may be arranged in a direction identical to the length direction of the strap 120, or may be arranged perpendicular to the length direction of the main body 110 or the length direction of the strap 120, i.e., to face each other, as illustrated in FIG. 3. Further, the first outer electrode 141 and the second outer electrode 142 may be disposed to face each other.

The first and second outer electrodes 141 and 142 may each have a half ring shape and may face each other with a gap therebetween. Herein, the term "half ring" may mean a "C" shape that is curved or angular. For example, the half ring may have an angular "C" shape having a half square/rectangle outline, as shown in FIG. 3.

In addition, although the first and second outer electrodes 141 and 142 shown in FIG. 3 are illustrated as angular half rings having a constant width, they are not limited thereto and may have different widths in different directions.

Once a user puts on the wrist-type body composition measuring apparatus 100 and touches the first and second outer electrodes 141 and 142 with a finger or a part of the palm, the measurer 111 applies an alternating current and measures a voltage to calculate body impedance, and the analyzer 112 analyzes body composition of the user by using the body impedance measured by the measurer 111.

As described above, in the wrist-type body composition measuring apparatus 100, the first and second outer electrodes 141 and 142, which contact a user during measurement of body composition, are mounted on the surface of the main body 110, rather than on the strap 120, such that the strap 120 may be readily changed, and a degree of freedom of the disposition of electrodes and aesthetic impression may be increased. Further, the first and second outer electrodes 141 and 142 are disposed close to each other to allow a user to touch them with a finger, such that body composition may be measured with only a finger or a part of the palm, enabling convenient measurement of body composition.

Upon applying a current through the first inner electrode 131 and the first outer electrode 141, the measurer 111 measures the voltage between the second inner electrode 132 and the second outer electrode 142 to measure body impedance.

Specifically, while the first and second inner electrodes 131 and 132 are in contact with a wrist, the first and second outer electrodes 141 and 142 are contacted with a user's finger or a part of the palm, such that the first outer electrode 141 and the first inner electrode 131 form a closed circuit through the user and the second outer electrode 142 and the second inner electrode 132 form a closed circuit through the user. Then, a sine wave alternating current is applied, and a voltage between the second outer electrode 142 and the second inner electrode 132 is measured, to calculate body impedance based on the applied current and the measured voltage.

As described above, in the case where body impedance is measured by using two inner electrodes and two outer electrodes, i.e., four electrodes, body impedance may be measured more accurately than the case where only two electrodes are used.

Figure 6:
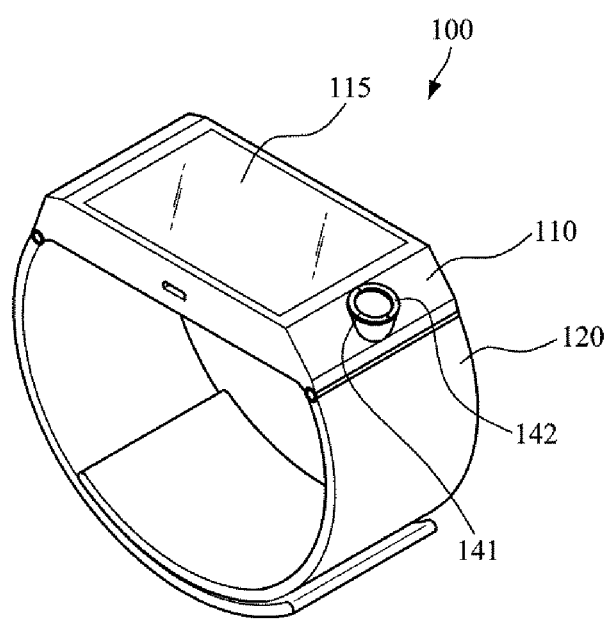
FIG. 6 is a perspective view of another example of the wrist-type body composition measuring apparatus.

FIG. 6 is a perspective view of another example of the wrist-type body composition measuring apparatus 100.

As illustrated in FIG. 6, the first outer electrode 141 and the second outer electrode 142 may each be a curved half ring having a semicircular shape, and may face each other with a gap therebetween to isolate them electrically.

In addition, although the first and second outer electrodes 141 and 142 shown in FIG. 6 are illustrated as half rings having a constant width, they may have different widths.

Figure 7:
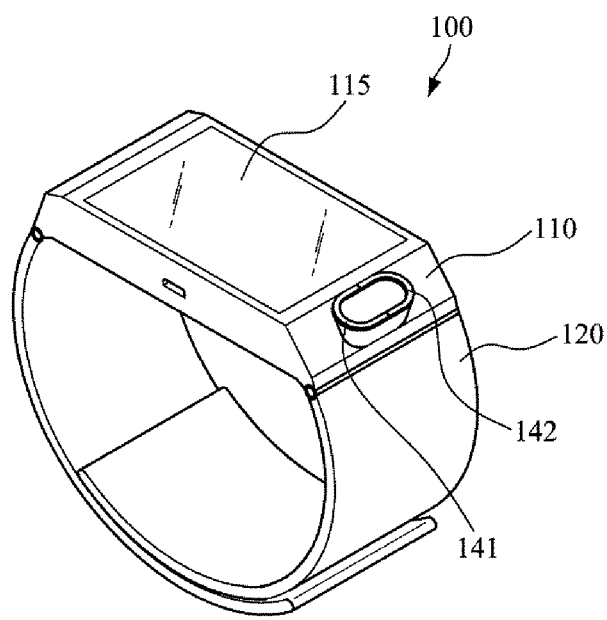
FIG. 7 is a perspective view of still another example of the wrist-type body composition measuring apparatus.

FIG. 7 is a perspective view of still a further example of the wrist-type body composition measuring apparatus 100.

As illustrated in FIG. 7, the first outer electrode 141 and the second outer electrode 142 may each be a half ring having a half semioval shape, a half semielliptical shape or a half rectangle with rounded corners shape (i.e., a half racetrack shape), and may face each other with a gap therebetween to isolate them electrically.

In addition, although the first and second outer electrodes 141 and 142 shown in FIG. 7 are illustrated as half rings having a constant width, they are not limited thereto and may be formed having different widths.

Figure 8:
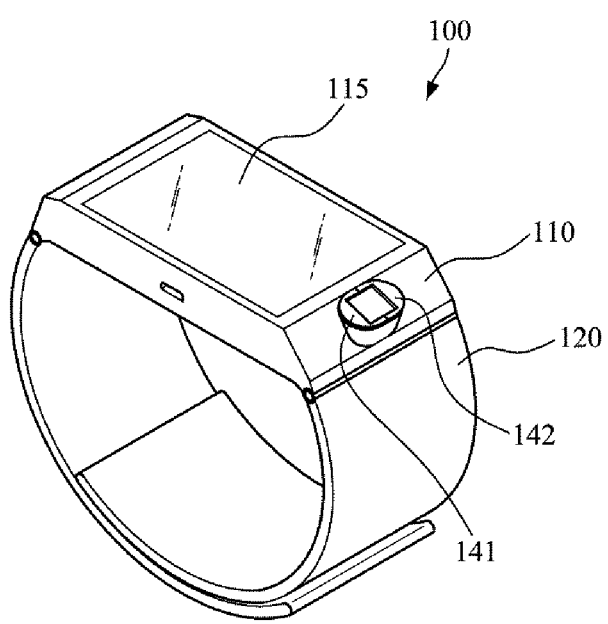
FIG. 8 is a perspective view of still a further example of the wrist-type body composition measuring apparatus.

FIG. 8 is a perspective view of still another example of the wrist-type body composition measuring apparatus 100.

As illustrated in FIG. 8, the first outer electrode 141 and the second outer electrode 142 may each be a half ring and may face each other with a gap therebetween. The inner portions of the first outer electrode 141 and the second outer electrode 142 facing each other may have a rectangular shape while the outer portions have a curved shape. The first and second outer electrodes 141 and 142 may thus form, for example, a polygonal space defined by the inner portions and having upper and lower openings provided by the gap.

Figure 9:
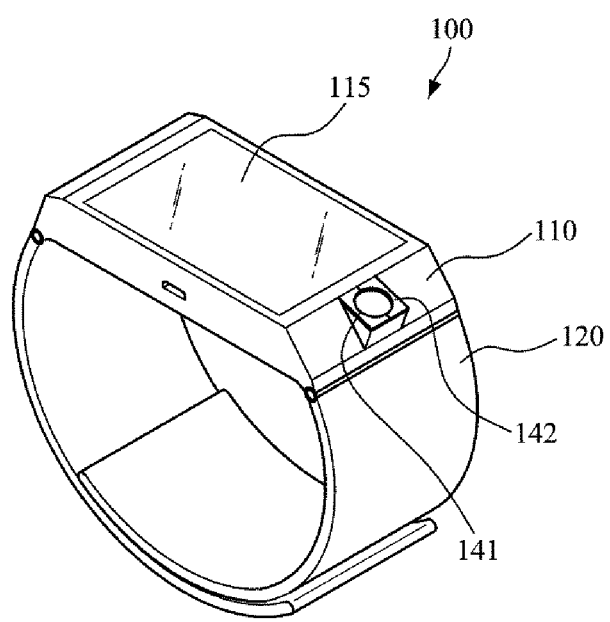
FIG. 9 is a perspective view of still another example of the wrist-type body composition measuring apparatus.

FIG. 9 is a perspective view of another example of the wrist-type body composition measuring apparatus 100.

As illustrated in FIG. 9, the first outer electrode 141 and the second outer electrode 142 may each be a half ring and may face each other with a gap therebetween. The inner portions of the first outer electrode 141 and the second outer electrode 142 facing each other may have a curved shape while the outer portions have a rectangular shape. The first and second outer electrodes 141 and 142 may thus form, for example, a circular space defined by the inner portions and having upper and lower openings provided by the gap.

Figure 10:
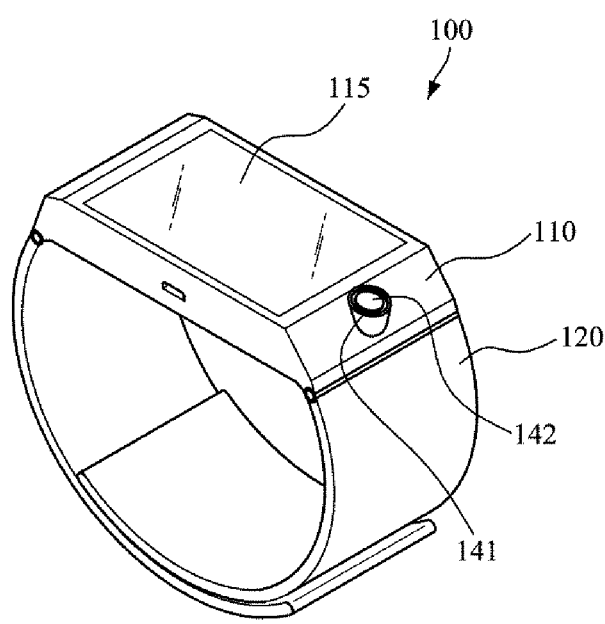
FIG. 10 is a perspective view of still another of the wrist-type body composition measuring apparatus.

FIG. 10 is a perspective view of another example of the wrist-type body composition measuring apparatus 100.

Referring to FIG. 10, the first and second outer electrodes 141 and 142 may be formed in such a manner that one electrode 141 surrounds the other electrode 142. Here, the first outer electrode 141 surrounds the second outer electrode 142, but an opposite configuration may also be implemented. Further, the first and second outer electrodes 141 and 142 may be formed to have the same center.

Figure 11:
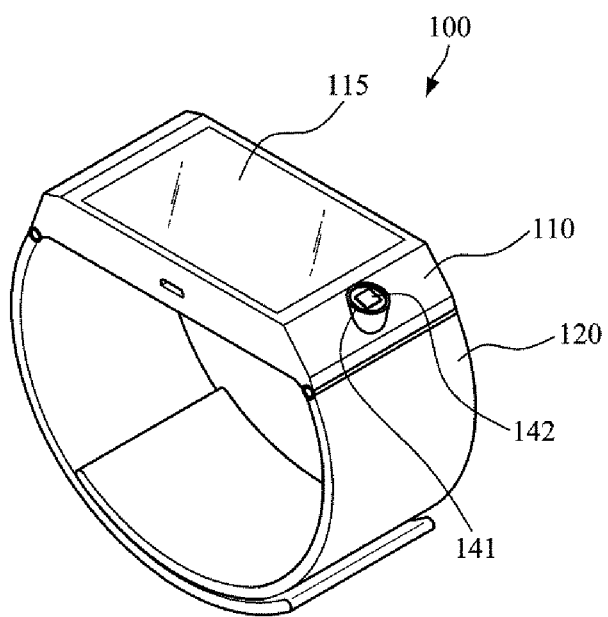
FIG. 11 is a perspective view of still another example of the wrist-type body composition measuring apparatus.

In another example, as in the wrist-type body composition measuring apparatus 100 illustrated in FIG. 11, one electrode 141 may surround the other electrode 142, and the two outer electrodes 141 and 142 may be formed to have the same center, in which the inner electrode may be in a square shape and the outer electrode may be in a circular shape. The inner electrode may be in a circular shape and the outer electrode may be in a square shape, and other shapes, rather than a square or circle, may also be applied.

Figure 12:
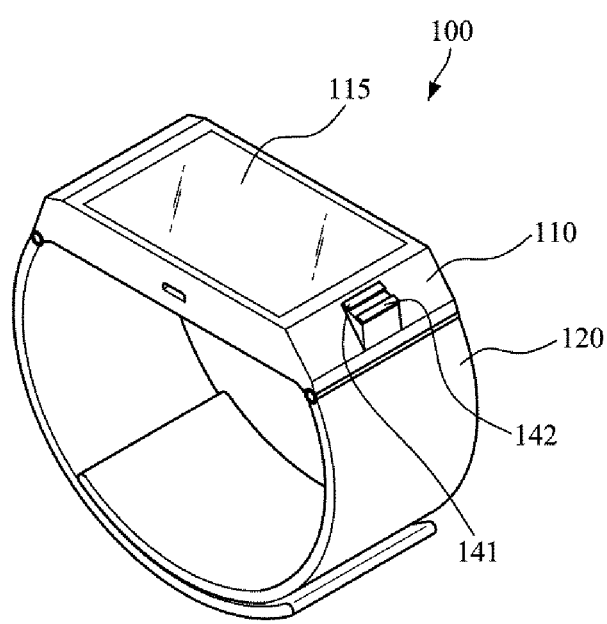
FIG. 12 is a perspective view of still another example of the wrist-type body composition measuring apparatus.

In addition, as in the wrist-type body composition measuring apparatus 100 illustrated in FIG. 12, the first and second outer electrodes 141 and 142 may be arranged symmetrical to each other. While FIG. 12 illustrates two symmetrical electrodes arranged in a direction identical to the length direction of the strap 120, the two symmetrical electrodes may be arranged perpendicular to the length direction of the strap 120, and may be in other shapes rather than a rectangular shape.

Figure 13:
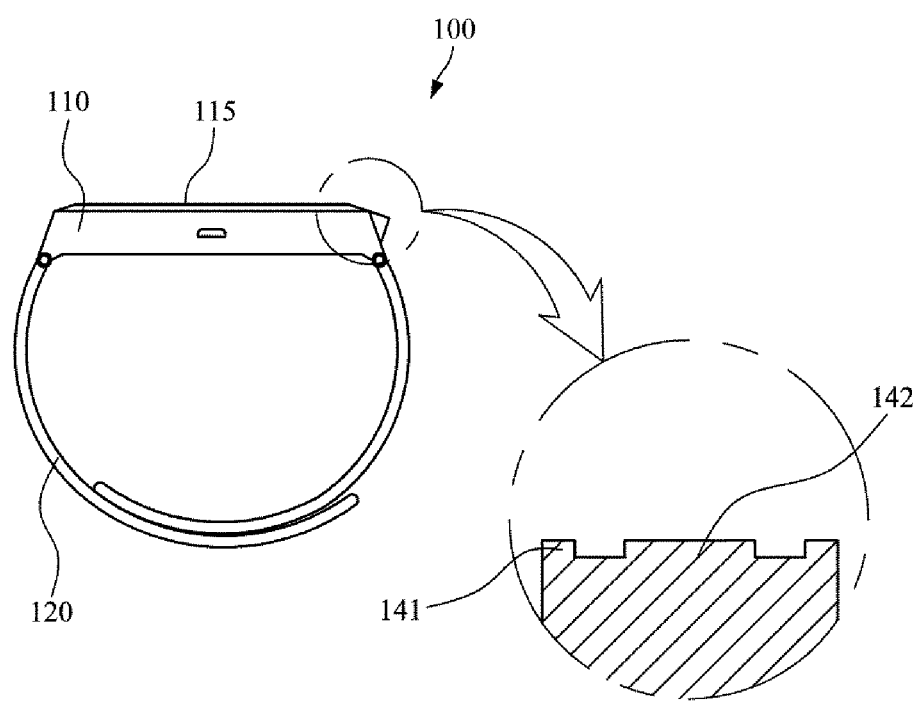
FIG. 13 is a cross-sectional view of an enlarged portion of the wrist-type body composition measuring apparatus illustrated in FIG. 10.

FIG. 13 is a cross-sectional view of the wrist-type body composition measuring apparatus 100 illustrated in FIG. 10. As illustrated in FIG. 13, upper surfaces of the first and second outer electrodes 141 and 142 may be formed on the same plane. In this case, when a finger or a part of the palm is contacted with the first and second outer electrodes 141 and 142, the contact may be made accurately.

In the aforementioned embodiments, the first and second outer electrodes 141 and 142 are formed on a lower front side of the main body 110, which is merely illustrative, and the first and second outer electrodes 141 and 142 may be formed on the upper side of the main body 110 or on the left or right side of the main body 110.

Further, the first and second outer electrodes 141 and 142 may be formed to be pressed, so as to operate as functional buttons that perform predetermined functions upon being pressed. That is, once the first and second outer electrodes are pressed, numbers are input or a screen is moved from side to side to enable a user to select a specific function.

Figure 14:
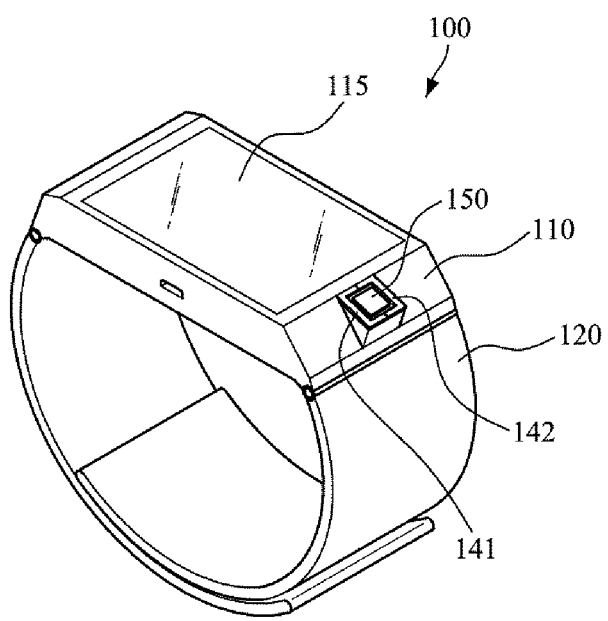
FIG. 14 is a perspective view of yet another example of the wrist-type body composition measuring apparatus.

FIG. 14 is a perspective view of yet another example of the wrist-type body composition measuring apparatus 100. Referring to FIG. 14, the wrist-type body composition measuring apparatus 100 may further include a bio-signal sensor 150. The bio-signal sensor 150 may be disposed between the first outer electrode 141 and the second outer electrode 142 inside the space defined by their inner portions and may collect a bio-signal of the user. In other words, the bio-signal sensor 150 may be surrounded by the first and second electrodes 141 and 142. The bio-signal sensor 150 may be an optical sensor, and more specifically, a photoplethysmogram (PPG) sensor.

Figure 15:
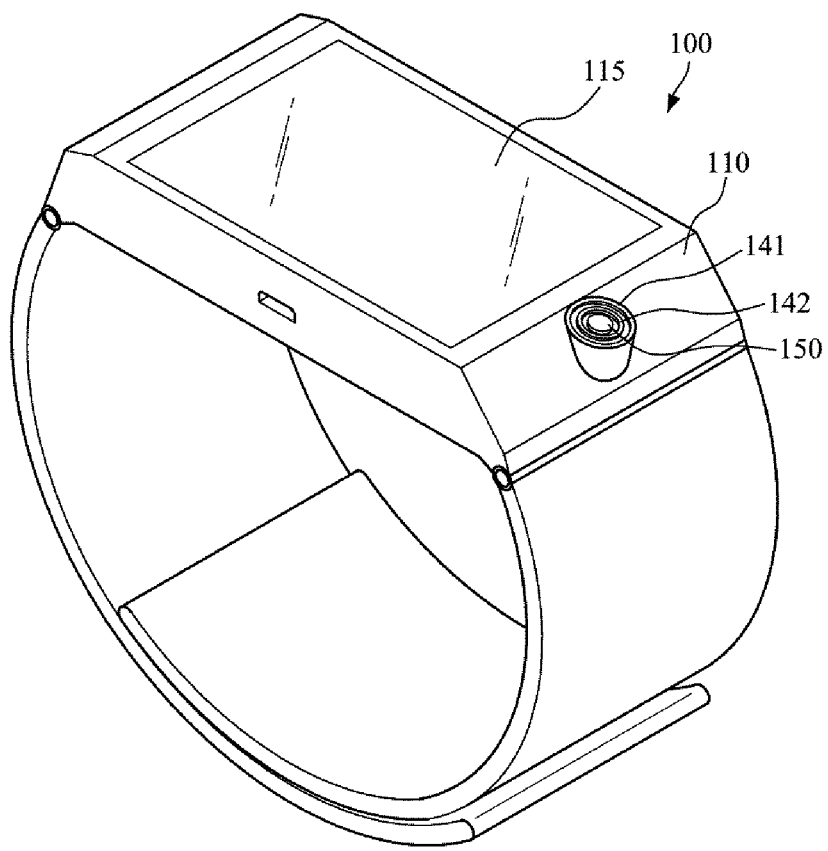
FIG. 15 is a perspective view of yet another example of the wrist-type body composition measuring apparatus.

FIG. 15 is a perspective view of yet another example of the wrist-type body composition measuring apparatus 100. Referring to FIG. 15, the bio signal sensor 150 may be disposed inside a space defined by the inner portion of the second outer electrode 142. The first outer electrode 141 may surround the second outer electrode 142 and the second outer electrode 142 in turn may surround the bio-signal sensor 150. Thus, the bio signal sensor 150 may be surrounded by both the first and second electrodes 141 and 142.

As shown, the first and second outer electrodes 141 and 142 may have a circular ring shape. However, their shape is not limited thereto, and the first and second outer electrodes may have other ring shapes. For example, the first and second outer electrodes 141 and 142 may have a rectangular ring shape, a lozenge-shaped ring shape, an elliptical ring shape, a triangular ring shape or the like. While the first and second outer electrodes 141 and 142 shown in FIG. 15 show rings with a constant width, they may be implemented in different embodiments with different widths. For example, the first and second outer electrodes 141 and 142 may have a ring shape having an angular inner portion and a curved outer portion. Alternatively, the first and second outer electrodes 141 and 142 may have a ring shape having a curved inner portion and an angular outer portion.

In another example, the first and second outer electrodes 141 and 142 may each have a different ring shape. For example, the first outer electrode 141 may have a circular ring shape, and the second outer electrode 142 may have a rectangular ring shape.

The bio-signal sensor 150 and the first and second outer electrodes 141 and 142 may have upper surfaces configured to contact a finger or a part of the palm simultaneously. For example, an upper surface of the bio-signal sensor 150 may be disposed on the same plane as upper surfaces of the first and second outer electrodes 141 and 142. However, embodiments are not limited to the above example, and the upper surface of the bio-signal sensor 150 may be formed above or below the upper surfaces of the first and second outer electrodes 141 and 142 if the height differences are not great enough to prevent a simultaneous touching by a finger or a part of the palm.

A bio-signal, for example a PPG signal, collected by the bio-signal sensor 150 may be transmitted to the analyzer 112 and biometric information of the user may be obtained from the bio-signal. The biometric information may include blood pressure, vascular age, arterial stiffness, aortic pressure waveform, stress index, fatigue, and the like, but is not limited thereto.

In the aforementioned example, the body impedance is measured using the first and second inner electrodes 131 and 132 and the first and second outer electrodes 141 and 142, and it is also possible to measure an electrocardiography (ECG) signal using these same electrodes.

Figure 16:
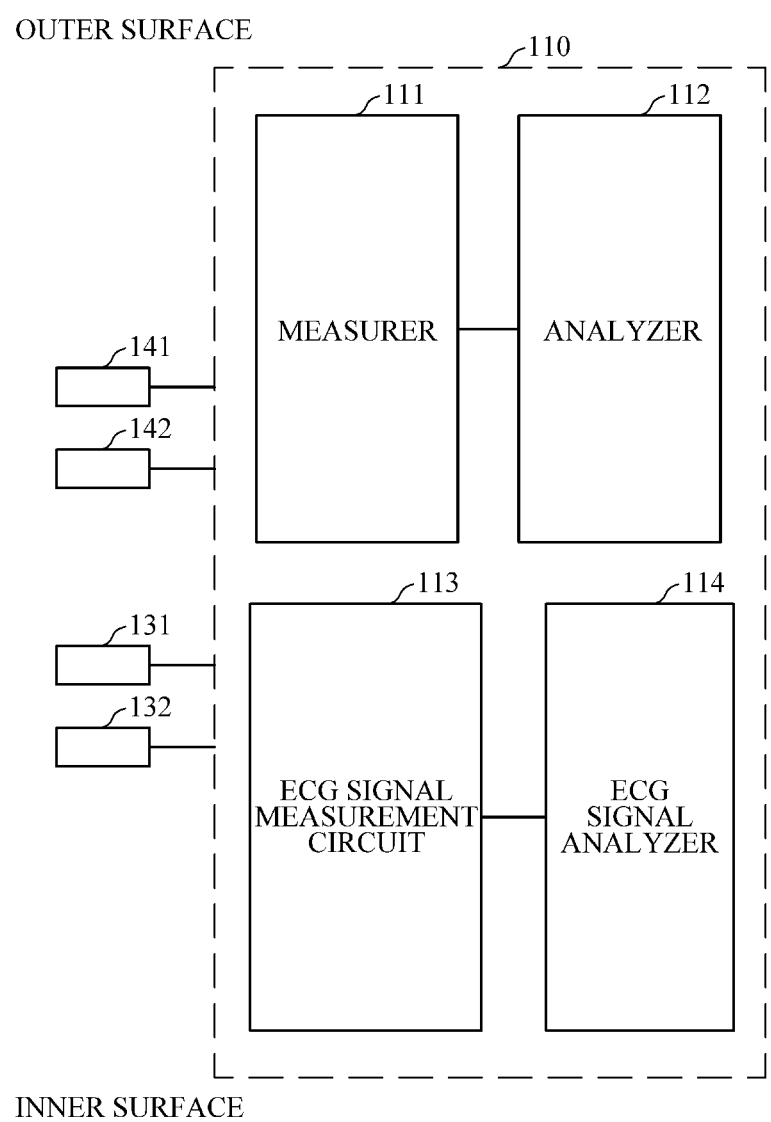
FIG. 16 is a block diagram illustrating another example of a wrist-type body composition measuring apparatus.

FIG. 16 is a block diagram illustrating another example of a wrist-type body composition measuring apparatus. As shown in FIG. 16, the main body 110 may further include an ECG signal measurement circuit 113 and an ECG signal analyzer 114 configured to analyze a measured ECG signal. The ECG signal measurement circuit 113 may measure the ECG signal through all or some of the first and second inner electrodes and the first and second outer electrodes. In other words, the ECG signal may be measured through at least three electrodes from among the first inner electrode 131, the second inner electrode 132, the first outer electrode 141 and the second outer electrode 142.

For example, in the case where the ECG signal is measured through three electrodes, the first inner electrode 131 may be used as a reference electrode, and either of the first and second outer electrodes 141 and 142 may be used as a positive electrode and the second inner electrode 132 as a negative electrode. Alternatively, the second inner electrode 132 may be used as a reference electrode and either of the first and second outer electrodes 141 and 142 may be used as a positive electrode and the first inner electrode 131 as a negative electrode. Here, the positive electrode and the negative electrode may be switched with each other.

In another example, in the case where the ECG signal is measured through four electrodes, the first and second outer electrodes 141 and 142 may be short-circuited to each other. Thus, the first inner electrode 131 may be used as a reference electrode, and the short-circuited first and second outer electrodes 141 and 142 may be used as a positive electrode and the second inner electrode 132 as a negative electrode. Alternatively, the second inner electrode 132 may be used as a reference electrode, and the short-circuited first and second outer electrodes 141 and 142 may be used as a positive electrode and the first inner electrode 131 as a negative electrode. Here, the positive electrode and the negative electrode may be switched with each other.

In addition, when a user wearing the above-described wrist-type body composition measuring apparatus 100 on his/her wrist touches the first outer electrode 141 and the second outer electrode 142 with one finger or a part of the palm, the wrist-type body composition measuring apparatus 100 may measure the body impedance along with the ECG signal.

When measuring the body impedance along with the ECG signal, the wrist-type body composition measuring apparatus 100 may continuously measure each of the body impedance and the ECG signal sequentially. For example, the measurer 111 measures the body impedance first and then the ECG signal measurement circuit 113 measures the ECG signal while one finger or a part of the palm of the user is contacted with the first and second outer electrodes 141 and 172. However, the sequence of measurement is not limited to the above example, and the body impedance may be measured after the ECG signal is measured.

A switch may be added to each electrode to allow the measurer 111 for measuring body impedance and the ECG signal measurement circuit 113 for measuring an ECG signal to share the electrodes with each other. In this case, both of the measurer 111 and the ECG signal measurement circuit 113 may be connected to the electrodes through the switches.

For example, the first inner electrode 132, the second inner electrode 132, the first outer electrode 141, and the second outer electrode 142 may be used for measuring body impedance, and the first and second inner electrodes 131 and 132 and the first outer electrode 141 may also be used for measuring an ECG signal. When the user wears the wrist-type body composition measuring apparatus 100 on his/her left wrist and touches the first and second outer electrodes 141 and 142 with a right-hand finger in order to measure a bio-signal, the switches connected to the first and second inner electrodes 131 and 132 and the switches connected to the first and second outer electrodes 141 and 142 may be connected to the measurer 111 during a measurement time T1. The body impedance measured by the measurer 111 is transmitted to the analyzer 112, and the analyzer 112 may analyze body composition using the body impedance.

After the measurement time T1 elapses, the switches connected to the first and second inner electrodes 131 and 132 and the first outer electrode 141 may be switched to the ECG signal measurement circuit 113. By doing so, the ECG signal measurement circuit 113 may be connected to the first and second inner electrodes 131 and 132 and the first outer electrode 141 through the switches, so that an ECG signal may be measured during a measurement time T2. The measured ECG signal is transmitted to the ECG signal analyzer 114 and the ECG signal analyzer 114 may analyze the biometric information of the user using the ECG signal.

The analyzer 112 and the ECG signal analyzer 114 may be integrated into a single module or chip. The analyzer 112 and the ECG signal analyzer 114 may each include an additional circuit for processing the signals transmitted from the measurer 111 and the ECG signal measurement circuit 113, or may be implemented as a software program and a processor to execute the program which converts the received signal into digital information and processes a resulting converted digital signal.

Further, although not illustrated herein, the main body 110 may include a wireless communicator. The wireless communicator may include a Bluetooth module, a Radio Frequency (RF) module, and the like. The wireless communicator may transmit body composition information, analyzed by the analyzer 112, to a smartphone and the like, thus enabling a user to check and manage the body composition information on their smartphone or the like.

The main body 110 may include a display 115. The display 115 is mounted in such a manner that a screen of the display 115 may be exposed to the outside of the main body 110. The display 115 displays the body composition information, analyzed by the analyzer 112, in numbers or characters to show the information to a user.

Similar to the aforementioned various exemplary embodiments of the first and second outer electrodes 141 and 142, the first and second inner electrodes 131 and 132 may be implemented in various embodiments. For example, the first and second inner electrodes 131 and 132 may be each formed as a half ring facing each other with a gap therebetween. In this case, the bio-signal sensor 150 may be disposed in a space between the first and second inner electrodes 131 and 132.

The wrist-type body composition measuring apparatus may measure body composition conveniently while being carried. Further, the wrist-type body composition measuring apparatus may increase a degree of freedom of the disposition of electrodes and aesthetic impression. In addition, the wrist-type body composition measuring apparatus may conveniently measure body composition by using only one finger or a part of the palm.

In the aforementioned description, the wrist-type body composition measuring apparatus 100 may be a wearable device, such as a smart watch or a smart band, which can be worn on a wrist of a user. However, the configuration included in the wrist-type body composition measuring apparatus 100 may be implemented as another wearable device that can be put on a different body part other than the wrist. For example, the wearable device may be implemented as a ring or a garment. The wearable device may include the first inner electrode 131, the second inner electrode 132, the first outer electrode 141, the second outer electrode 142, the bio-signal sensor 150, the measurer 111, and the analyzer 112, which are all described above.

In another example, the configuration included in the wrist-type body composition measuring apparatus 100 may be implemented in a portable device, such as a smartphone. For example, the first and second outer electrodes 141 and 142 may be formed on one surface of a portable device, and the first and second inner electrodes 131 and 132 may be formed on another surface of the portable device.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wrist-type apparatus comprising:
   a main body; and
   a strap connected to the main body and configured to be flexible,
   wherein the main body comprises:
      a display disposed on a front-facing surface of the main body;

a photoplethysmogram (PPG) sensor configured to detect a PPG signal and disposed on the front-facing surface of the main body to be in contact with a single finger of a user during measurement of biometric information;
an electrocardiography (ECG) sensor comprising:
a first inner ECG electrode and a second inner ECG electrode which are provided on a rear surface of the main body to be in direct contact with a wrist of the user; and
at least one outer ECG electrode disposed on the front-facing surface of the main body to be in contact with the single finger of the user at a same time when the PPG sensor is touched by the single finger, wherein the ECG sensor is configured to detect an ECG signal from the single finger in contact with the at least one outer ECG electrode of the ECG sensor and the wrist by using the first inner ECG electrode as a reference electrode, using the second inner ECG electrode as one of a positive electrode and a negative electrode, and the at least one outer ECG electrode as another of the positive electrode and the negative electrode; and
a processor configured to analyze the biometric information of the user using the PPG signal and the ECG signal,
wherein the front-facing surface of the main body comprises a first area in which the display is disposed, and a second area which is arranged side-by-side with the first area, and in which a contact surface of the PPG sensor and a contact surface of the at least one outer ECG electrode are spaced apart from each other and arranged to be simultaneously touched by the single finger,
wherein the entire contact surface of the PPG sensor and the entire contact surface of the at least one outer ECG electrode are disposed at a same perpendicular distance from the rear surface of the main body,
wherein the contact surface of the PPG sensor and the contact surface of the at least one outer ECG electrode are arranged and sized such that a majority of the entire contact surface of the PPG sensor and a majority of the entire contact surface of the at least one outer ECG electrode are covered by the single finger when simultaneously touched by the single finger,
wherein the PPG sensor and the at least one outer ECG electrode are disposed apart from each other and disposed directly on the front-facing surface of the main body, and
wherein the front-facing surface is directly exposed to an outside of the wrist-type apparatus, through a gap between the PPG sensor and the at least one outer ECG electrode.

2. The wrist-type apparatus of claim 1, wherein the at least one outer ECG electrode comprises a first outer ECG electrode and a second outer ECG electrode, and the processor is further configured to
control a body fat measurement by measuring a voltage through the second inner ECG electrode and the second outer ECG electrode to measure body impedance of the user when current is applied to the first inner ECG electrode and the first outer ECG electrode, in a first measurement mode, and
control an ECG measurement by short-circuiting the first outer ECG electrode and the second outer ECG electrode, and using the short-circuited first outer ECG electrode and the second outer ECG electrode as the positive electrode or the negative electrode, in a second measurement mode.

3. The wrist-type apparatus of claim 1, wherein the at least one outer ECG electrode comprises a first outer ECG electrode and a second outer ECG electrode, and
wherein the first outer ECG electrode and the second outer ECG electrode are each formed as a half ring and face each other with a gap therebetween, and the half ring has an angular C shape.

4. The wrist-type apparatus of claim 1, wherein the at least one outer ECG electrode comprises a first outer ECG electrode and a second outer ECG electrode, and
the first outer ECG electrode and the second outer ECG electrode are each formed as a half ring and face each other with a gap therebetween, and the half ring has a semicircular shape.

5. The wrist-type apparatus of claim 1, wherein the at least one outer ECG electrode comprises a first outer ECG electrode and a second outer ECG electrode, and
wherein the first outer ECG electrode and the second outer ECG electrode are each formed as a half ring and face each other with a gap therebetween, and the half ring has a semielliptical or semioval shape.

6. The wrist-type apparatus of claim 1, wherein the at least one outer ECG electrode comprises a first outer ECG electrode and a second outer ECG electrode, wherein an inner portion of a half ring has an angular shape and an outer portion of the half ring has a curved shape.

7. The wrist-type apparatus of claim 1, wherein the at least one outer ECG electrode comprises a first outer ECG electrode and a second outer ECG electrode,
wherein the first outer ECG electrode the second outer ECG electrode are each formed as a half ring, and
wherein an inner portion of the half ring has a curved shape and an outer portion of the half ring has an angular shape.

8. The wrist-type apparatus of claim 1, wherein the at least one outer ECG electrode comprises a first outer ECG electrode and a second outer ECG electrode, and
wherein an arrangement direction of the first inner ECG electrode and the second inner ECG electrode and an arrangement direction of the first and second outer ECG electrodes are perpendicular to a length direction of the strap.

9. The wrist-type apparatus of claim 1, wherein the at least one outer ECG electrode comprises a first outer ECG electrode and a second outer ECG electrode, and
wherein an arrangement direction of the first inner ECG electrode and the second inner ECG electrode and an arrangement direction of the first and second outer ECG electrodes are identical to a length direction of the strap.

10. The wrist-type apparatus of claim 1, wherein the at least one outer ECG electrode comprises a first outer ECG electrode and a second outer ECG electrode,
wherein one of a first arrangement direction of the first inner ECG electrode and the second inner ECG electrode and a second arrangement direction of the first and second outer ECG electrodes is identical to a length direction of the strap, and
the first arrangement direction is perpendicular to the second arrangement direction.

11. The wrist-type apparatus of claim 1, wherein the main body comprises a first measurement circuit configured to measure a body fat of the user, wherein the ECG sensor comprises a second measurement circuit configured to measure the ECG signal; and wherein the first measurement circuit and the second measurement circuit share the first inner ECG electrode, the second inner ECG electrode, and the at least one outer ECG electrode via switching operations.

12. The wrist-type apparatus of claim 1, wherein the at least one outer ECG electrode comprises a first outer ECG electrode and a second outer ECG electrode, and wherein the first and second outer ECG electrodes are configured to operate as buttons to perform predetermined functions when the first outer ECG electrode and the second outer ECG electrode are pressed.

13. The wrist-type apparatus of claim 1, wherein the first inner ECG electrode and the second inner ECG electrode of the ECG sensor are arranged side-by-side in a direction perpendicular to a direction in which the strap extends.

14. A wearable device comprising:

a display disposed on a front-facing surface of the wearable device;

a photoplethysmogram (PPG) sensor disposed on the front-facing surface and configured to detect a PPG signal;

an electrocardiography (ECG) sensor comprising:
 a first ECG electrode and a second ECG electrode disposed on a rear surface of the wearable device; and
 a third ECG electrode that is arranged on the front-facing surface to oppose the first ECG electrode and the second ECG electrode,
 wherein the ECG sensor is configured to detect an ECG signal from a single finger and a wrist of a user when the wearable device is worn around the wrist; and a processor configured to analyze biometric information of the user using the PPG signal and the ECG signal, wherein the front-facing surface of the wearable device comprises a first area in which the display is disposed, and a second area which is arranged side-by-side with the first area, and in which a contact surface of the PPG sensor and a contact surface of the third ECG electrode are arranged to be simultaneously touched by the single finger, wherein the entire contact surface of the PPG sensor and the entire contact surface of the third ECG electrode are disposed at a same perpendicular distance from the rear surface of the wearable device, wherein the contact surface of the PPG sensor and the contact surface of the third ECG electrode are arranged and sized such that a majority of the entire contact surface of the PPG sensor and a majority of the entire contact surface of the third ECG electrode are covered by the single finger when simultaneously touched by the single finger, wherein the PPG sensor and the third ECG electrode are disposed apart from each other and disposed directly on the front-facing surface, and wherein the front-facing surface is directly exposed to an outside of the wearable device, through a gap between the PPG sensor and the third ECG electrode.

15. The wearable device of claim 14, wherein the first ECG electrode and the second ECG electrode face each other with a gap therebetween.

16. The wearable device of claim 15, wherein the first ECG electrode and the second ECG electrode have an angular C-shape, semicircular shape, or semielliptical shape.

17. The wearable device of claim 14, wherein the ECG sensor is further configured to detect the ECG signal by using the first ECG electrode as a reference electrode, using the second ECG electrode as one of a positive electrode and a negative electrode, and the third ECG electrode as another of the positive electrode and the negative electrode.

18. A wrist-type apparatus comprising:

a main body; and a strap connected to the main body and configured to be flexible, wherein the main body comprises:
 a display disposed on a front-facing surface of the main body;
 a photoplethysmogram (PPG) sensor configured to detect a PPG signal and disposed on the front-facing surface of the main body to be in contact with a single finger of a user during measurement of biometric information;
 an electrocardiography (ECG) sensor comprising:
  a first inner ECG electrode and a second inner ECG electrode which are provided on a rear surface of the main body to be in direct contact with a wrist of the user; and
  at least one outer ECG electrode disposed on the front-facing surface of the main body to be in contact with the single finger of the user at a same time when the PPG sensor is touched by the single finger, wherein the ECG sensor is configured to detect an ECG signal from the single finger in contact with the at least one outer ECG electrode of the ECG sensor and the wrist by using the first inner ECG electrode as a reference electrode, using the second inner ECG electrode as one of a positive electrode and a negative electrode, and the at least one outer ECG electrode as another of the positive electrode and the negative electrode; and
 a processor configured to analyze the biometric information of the user using the PPG signal and the ECG signal, wherein the front-facing surface of the main body comprises a first area in which the display is disposed, and a second area which is arranged side-by-side with the first area, and in which a contact surface of the PPG sensor and a contact surface of the at least one outer ECG electrode are arranged to be simultaneously touched by the single finger, wherein the entire contact surface of the PPG sensor and the entire contact surface of the at least one outer ECG electrode are disposed at a same perpendicular distance from the rear surface of the main body, wherein the contact surface of the PPG sensor and the contact surface of the at least one outer ECG electrode are configured such that the entire contact surface of the PPG sensor and the entire contact surface of the at least one outer ECG electrode are covered by the single finger when simultaneously touched by the single finger, wherein the PPG sensor and the at least one outer ECG electrode are disposed apart from each other and disposed directly on the front-facing surface of the main body, and wherein the front-facing surface is directly exposed to an outside of the wrist-type apparatus, through a gap between the PPG sensor and the at least one outer ECG electrode.

\* \* \* \* \*